United States Patent
Roehrich

(10) Patent No.: US 10,413,512 B2
(45) Date of Patent: Sep. 17, 2019

(54) NICOTINE-CONTAINING GRANULATE

(75) Inventor: Tillmann Roehrich, Rheinfelden (CH)

(73) Assignee: SIEGFRIED LTD., Zofingen (CH)

( * ) Notice: Subject to any disclaimer, the term of this patent is extended or adjusted under 35 U.S.C. 154(b) by 1047 days.

(21) Appl. No.: 13/058,769

(22) PCT Filed: Sep. 16, 2009

(86) PCT No.: PCT/EP2009/006676
§ 371 (c)(1),
(2), (4) Date: Mar. 14, 2011

(87) PCT Pub. No.: WO2010/031536
PCT Pub. Date: Mar. 25, 2010

(65) Prior Publication Data
US 2011/0165253 A1    Jul. 7, 2011

(30) Foreign Application Priority Data

Sep. 17, 2008   (EP) ..................................... 08016336

(51) Int. Cl.
| | | |
|---|---|---|
| *A61K 31/465* | (2006.01) | |
| *A61K 9/14* | (2006.01) | |
| *A61P 25/34* | (2006.01) | |
| *B29B 9/08* | (2006.01) | |
| *B29B 9/12* | (2006.01) | |
| *A61K 9/16* | (2006.01) | |

(52) U.S. Cl.
CPC .......... *A61K 9/1623* (2013.01); *A61K 9/1635* (2013.01)

(58) Field of Classification Search
None
See application file for complete search history.

(56) References Cited

U.S. PATENT DOCUMENTS

| | | | |
|---|---|---|---|
| 5,135,753 A | * | 8/1992 | Baker et al. .................. 424/435 |
| 2001/0019763 A1 | * | 9/2001 | Hafermann et al. ....... 428/313.5 |
| 2004/0191322 A1 | * | 9/2004 | Hansson ....................... 424/489 |

FOREIGN PATENT DOCUMENTS

| | | |
|---|---|---|
| EP | 1 578 422 B1 | 4/2007 |
| EP | 1 803 444 A2 | 7/2007 |
| FR | 2 792 200 A1 | 10/2000 |
| WO | WO 90/14821 A1 | 12/1990 |
| WO | WO 91/09599 A1 | 7/1991 |
| WO | WO 01/19208 A1 | 3/2001 |
| WO | WO 02/076605 A1 | 10/2002 |
| WO | WO 2007/133141 A1 | 11/2007 |
| WO | WO 2008/012071 A2 | 1/2008 |

OTHER PUBLICATIONS

English translation of FR2792200 (Oct. 20, 2000).*
Gereg et al. (Pharmaceutical Technology Tableting & Granulation 2002).*
Liu et al. (International Journal of Pharmaceutics 362 (2008) 109-117).*
Bulk Density of Powders Made Easy (obtained from <http://www.brookfieldengineering.com/download/files/Bulk_Density_of_Powders.pdf> on Sep. 4, 2015).*
International Search Report in International Application No. PCT/EP2009/006676; dated Feb. 1, 2010.

* cited by examiner

*Primary Examiner* — David J Blanchard
*Assistant Examiner* — Garen Gotfredson
(74) *Attorney, Agent, or Firm* — Oliff PLC

(57) ABSTRACT

A dust-reduced nicotine-containing granulate comprising a homogenous mixture of nicotine or a pharmaceutically acceptable nicotine derivative and an excipient, the granulate having a particle size of at least 150 μm. Method for the preparation of a dust-reduced nicotine-containing granulate, and use of the nicotine-containing granulate for the preparation of pharmaceutical products.

19 Claims, No Drawings

NICOTINE-CONTAINING GRANULATE

The present invention relates to a nicotine-containing granulate, a method for the production thereof, and its use for the preparation of a nicotine-containing pharmaceutical product.

Nicotine, or (S)-3-(1-Methyl-2-pyrrolidinyl)pyridine, is an alkaloid found in the nightshade family of plants (*Solanaceae*), predominantly in tobacco and coca, and in lower quantities in tomato, potato, eggplant, and green pepper. Nicotine has been found to constitute approximately 0.6-3.0% of dry weight of tobacco, with biosynthesis taking place in the roots, and accumulating in the leaves. It functions as an antiherbivore chemical, being a potent neurotoxin with particular specificity to insects; therefore, nicotine was widely used as an insecticide in the past.

Nicotine is a hygroscopic, oily, colorless or pale yellow liquid, which is miscible with water in its base form. It is characterized by a pyridine odor, a molecular weight of about 162 g/mol, an octanol:water partition coefficient (log P) of about 1.2, dissociation constants $pK_1$ of 6.16 and $pK_2$ of 10.96, and a melting point of approximately −79° C. As a nitrogenous base, nicotine forms salts with acids, which are usually solid and water soluble.

Nicotine and nicotine derivatives are readily absorbed from the gastro-intestinal tract, the buccal mucosa, the respiratory tract, and intact skin, and widely distributed throughout the tissues. Nicotine undergoes extensive first-pass metabolism when administered orally, thus reducing the bioavailability. Oral bioavailability of nicotine is about 30%. Furthermore, nicotine easily penetrates the skin. As nicotine enters the body, it is distributed quickly through the bloodstream and can cross the blood-brain barrier. The half life of nicotine in the body is around two hours. It is metabolized in the liver by cytochrome P450 enzymes, a major metabolite being cotinine.

In low concentrations (an average cigarette yields about 1 mg of absorbed nicotine), the substance acts as a stimulant in mammals and is one of the main factors responsible for the dependence-forming properties of tobacco smoking. Nicotine binds stereo-selectively to nicotinic-cholinergic receptors on autonomic ganglia, the adrenal medulla, neuromuscular junctions, and in the brain. It exerts two effects, a stimulant effect exerted at the locus ceruleus and a reward effect in the limbic system: By binding to CNS type nicotinic receptors, nicotine increases dopamine levels in the reward circuits of the brain. In this way, it activates the sympathetic nervous system and generates feelings of pleasure. Binding of nicotine to ganglion type nicotinic receptors, on the other hand, increases flow of adrenaline, a stimulating hormone. The release of adrenaline causes an increase in heart rate, blood pressure, and respiration, as well as higher blood glucose levels. Nicotine is a highly addictive substance. In high doses, nicotine will cause blocking of the nicotinic acetylcholine receptor, which is the reason for its toxicity and its effectiveness as an insecticide.

The primary therapeutic use of nicotine and nicotine derivatives is in treating nicotine dependence in order to cease smoking. Controlled levels of nicotine or a nicotine derivative are given to patients through gums, dermal patches, creams, lozenges, electric/substitute cigarettes or nasal sprays in an effort to wean them off their dependence. Nicotine has also been found therapeutically valuable in the treatment of other conditions involving release of dopamine, such as attention deficit hyperactive disorder (ADHD), attention deficit disorder (ADD), Tourette's syndrome, schizophrenia, Alzheimer's disease, Parkinson's disease, ulcerative colitis, anxiety, and depression; in the therapeutic angiogenesis and vasculogenesis; in the treatment of inflammatory bowel disease and autosomal dominant nocturnal frontal lobe epilepsy. Nicotine inhalers and patches are mainly used to treat smoking withdrawal syndrome.

Nicotine in its base form is readily absorbed through oral mucosa but is highly volatile and subject to oxidative degradation. By the action of air or light, nicotine is oxidized and turns brown. Due to its high toxicity, its low stability and its strong odor, handling of pure nicotine is highly demanding. Furthermore, the protection of staff and environment make great demands on the production, transport and storage equipment.

In order to circumvent these problems, several alternatives to nicotine in its base form have been developed. Especially (pharmaceutically acceptable) nicotine salts and complexes offer great advantages: The available nicotine salts are more stable compounds and are not as readily absorbed as the free base. They are usually solid, stable and have a low vapor pressure.

WO 2008/012071 discloses compositions, in particular gels comprising pharmaceutically acceptable salts of nicotine, for transdermal or transmucosal delivery of nicotine.

According to WO 02/076605, nicotine may be encapsulated as a core material in a film-forming polymer, such as vinylcaprolactone, vinylpyrrolidone or vinylacetate, and the thus obtained encapsulations may be used for releasing nicotine.

EP-A-1 803 444 and EP-A-1 578 422 relate to a particulate material formed of microcrystalline cellulose. Sorption of nicotine or a dissolved nicotine salt on microcrystalline cellulose particles results in a particulate material with a fast nicotine-release in vitro.

WO 90/14821 discloses a fructose-based granulated product suitable for the manufacture of tablets, which may be used in so-called energy tablets or confectionary tablets, as well as in the pharmaceutical industry.

WO 01/19208 relates to a method for producing agglomerates and tablets containing isomaltulose and/or hydrogenated isomaltulose by spray drying. The agglomerates may be used for the preparation of comprimates suitable for oral delivery of pharmaceutically active substances, such as nicotine.

However, these solid nicotine derivatives have a high tendency to raise dust during production and processing. This dust is highly mucosa-irritating and very aggressive. It is also very toxic and highly efficient if taken up in larger amounts via the gastrointestinal or respiratory tract. The processing of pure nicotine salts therefore requires elaborate and cost-intensive protection of staff and environment. In order to reduce the formation of dust during the production of the various pharmaceutical forms, special cautionary and protective measures are necessary, in particular with regard to machinery equipment. Typically, nicotine derivatives are processed in a closed containment. But once the production is finished, the containment needs to be thoroughly cleaned, leading to a demanding cleaning effort.

For these reasons, there is a demand for solid nicotine-containing products, which are "dust-reduced" or "dust-free", meaning that the dust formation during their production and processing is significantly reduced or even fully eliminated, thus allowing for easier handling and less elaborate equipment.

Therefore, it is a problem of the present invention to provide a solid nicotine-containing product, which is "dust-reduced" or, even better, "dust-free". It is a further problem of the present invention to provide a safe and simple method for the production of such a dust-free nicotine-containing material.

The problems are solved by the granulate according to claim 1, the method according to claim 9, and the use of the granulate of the present invention according to claims 13 to 15. Further preferred embodiments are subject to dependent claims.

The present invention provides a nicotine-containing granulate comprising a homogenous mixture of 1-50 wt % of nicotine or a pharmaceutically acceptable nicotine derivative and 50-99 wt % of an excipient, the granulate having a particle size of at least 150 μm. Throughout this application, the term "nicotine derivative" is meant to include any compound directly derived from nicotine, including, in particular, all nicotine salts. The particle size of the granulate is determined by sieve analysis.

A nicotine-containing granulate with a particle size of at least 150 μm is "dust-reduced" or even "dust-free": The formation of dust during production and processing is at least significantly reduced, preferably even fully eliminated. Thanks to the excipient, the cohesion of the granulate particles is guaranteed and therefore the break up of particles and formation of dust are effectively avoided.

The production, handling, and processing of the nicotine-containing granulate according to the present invention is much safer and less demanding than for the previously known products. By avoiding the formation of dust, the risk for staff and environment is significantly reduced, as the spreading of the highly toxic material is hampered. There is no dispersed, free flowing nicotine-containing material, which would be easily spread through air and taken up via skin, the gastrointestinal or the respiratory tract. The safety measures necessary during the production and storage of the nicotine-containing product according to the present invention, as well as during its further processing, are therefore also significantly reduced.

Furthermore, the nicotine-containing granulate according to the present invention has very favorable flow properties, thus rendering the granulate easily transferable from one container to another. The granulate of the present invention has typically a bulk density of at least 0.5 g/ml, an angle of repose of up to 35°, and a flow rate of at least 3 g/s. Furthermore, the dosage of the granulate is especially simple, making the preparation of pharmaceutical products, which need to have an exact nicotine content, from the nicotine-containing granulate of the present invention very advantageous.

In addition, the granulate of the present invention comprises a homogenous mixture of nicotine or the nicotine derivative with the excipient. This homogeneity is achieved by mixing all components prior to the granulate formation. Previously known methods, such as treatment of a base material granulate with nicotine or a nicotine derivative, do not provide a granulate, wherein the components are homogeneously mixed: Since the base material granulate has to be soaked with nicotine or a solution of a nicotine derivative, it cannot be guaranteed that the liquid is evenly distributed among the base material particles, nor that the single particles are thoroughly and evenly charged with the liquid. The granulate of the present invention, on the other hand, comprises a homogenous mixture of nicotine or the nicotine derivative with the excipient. For this reason, the exact nicotine-content of a certain amount of the granulate material is easily determined based on the original weight ratios, and no fluctuations due to non-uniform distribution of the nicotine or nicotine derivative have to be taken into account.

The nicotine-containing granulate according to the present invention may be produced by any method typically used for the preparation of a granulate, such as compacting or spray granulation. The granulate material is obtained from a homogenous mixture of nicotine or the pharmaceutically acceptable nicotine derivative with the excipient, optionally also comprising additives and/or solvents, preferably by compacting of the mixture and subsequent screening. If a solvent is added, it is preferably water. Alternatively, ethanol or other pharmaceutically acceptable solvents may be used.

In a preferred embodiment, the nicotine-containing granulate has a particle size of at least 500 μm. Granulate particles of this size are even less prone to raise dust, therefore making the processing of the granulate even more safe and less complicated.

Depending on the further processing of the nicotine-containing granulate, a granulate having a particle size of less than 2000 μm may be preferred, more preferably less than 1000 μm.

It may further be advantageous to have a nicotine-containing granulate with an equal particle size distribution, thus having a limited range of particle sizes. In another preferred embodiment, the nicotine-containing granulate has a particle size of 150 μm to 2000 μm, more preferably of 500 μm to 1000 μm.

According to a preferred embodiment, the nicotine-containing granulate comprises 10-30 wt % of nicotine or the pharmaceutically acceptable nicotine derivative and 70-90 wt %, for instance 80 wt %, of the excipient.

The nicotine-containing granulate according to the present invention comprises nicotine or a pharmaceutically acceptable nicotine derivative. Thus, the granulate can be used for the preparation of pharmaceutical compositions. In a preferred embodiment, the pharmaceutically acceptable nicotine derivative is a solid nicotine derivative, in particular a nicotine salt or a nicotine containing complex. The pharmaceutically acceptable nicotine derivative is preferably selected from the group consisting of nicotine bitartrate, nicotine polacrilin, nicotine betadex, nicotine polacrilex, and combinations thereof. These nicotine derivatives are well known. Alternatively, the nicotine salt may also be the salt of an acid selected from the group consisting of hydrochloric acid, hydrobromic acid, nitric acid, sulfonic acid, sulfuric acid, maleic acid, phosphoric acid, benzene sulfonic acid, methane sulfonic acid, acetic acid, propionic acid, butyric acid, citric acid, succinic acid, glycolic acid, gluconic acid, glucuronic acid, hexanioc acid, pentanoic acid, heptanoic acid, levulinic acid, lactic acid, malic acid, pyruvic acid, tartronic acid, and fumaric acid.

The excipient comprised in the nicotine-containing granulate according to the present invention is preferably a pharmaceutically acceptable material, more preferably one that is suited for use in a pharmaceutical product intended for oral or transdermal administration. According to a preferred embodiment, the excipient is selected from the group consisting of monosaccharides, disaccharides, hydrated or non-hydrated oligosaccharides, monosaccharide alcohols, disaccharide alcohols, starch, starch derivatives, cellulose, cellulose derivatives, insulin, sugar alcohols, calcium carbonate, calcium hydrogenphosphate, maltodextrins, polysaccharides, and combinations thereof. These preferred excipients are particularly well suited for oral administration. In a particularly preferred embodiment, the excipient and also the derived nicotine-containing granulate are sugar-free and thus suitable for the treatment of diabetic patients.

In addition, the use of such a sugar-free excipient significantly lowers the calorific value of the nicotine-containing product.

The excipient for the nicotine-containing granulate material is preferably selected from the group consisting of saccharose, lactose, glucose, fructose, xylose, starch, sorbit, mannit, xylit, sugar alcohols, cellulose, MicroceLac® (a spray composite material consisting of 75% lactose monohydrate and 25% microcrystalline cellulose, available from Meggle), Cellactose®, ProSolv® (a spray composite material consisting of 98% microcrystalline cellulose and 2% colloidal silicium dioxide, available from Rettenmeier & Söhne GmbH+ CO. KG), calcium carbonate, calcium hydrogenphosphate, maltodextrin, and combinations thereof.

In a further embodiment, the nicotine-containing granulate additionally comprises additives, such as sweeteners, binding agents, separating agents, lubricants, coloring agents, flavor additives, acids, effervescent agents, antioxidants, glidants and/or preservatives. The integration of additives directly into the granulate allows for the simplification of the further processing of the product, possibly to a pharmaceutical product. Examples of sweeteners, which may be comprised in the nicotine-containing granulate material, are aspartame, cyclamate, glycyrrhizin, thaumatin or saccharin; as flavor additives, e.g. lemon or mint aroma may be comprised; suitable acids include ascorbic acid or acetic acid; as lubricants, fatty acids or fatty acid salts may be comprised, such as magnesium stearate or sodium stearylfumarate; examples for effervescent agents are, for instance, bicarbonate or carbonate, as an antioxidant, butylhydroxytoluene, butylhydroxyanisol, ascorbic acid or vitamin E may be used, examples for glidants are colloidal silicium dioxide, calcium silicate or magnesium stearate, and as preservatives, p-hydroxybenzoic acid methyl ester, p-hydroxybenzoic acid ethyl ester, sorbic acid or benzoic acid may be comprised.

In a further aspect, the present invention provides a method for producing a nicotine-containing granulate. This method comprises the steps of
(a) mixing nicotine or a pharmaceutically acceptable nicotine derivative with an excipient;
(b) compacting the mixture obtained in step (a) in a roller compactor to produce granules; and
(c) screening the granules obtained in step (b) to remove particles, which are smaller than 150 μm.

The method according to the present invention allows for a simple, economically and ecologically advantageous production of a nicotine-containing granulate. Nicotine or a pharmaceutically acceptable nicotine derivative are directly mixed with the excipient, and optionally also with additives and/or a solvent, and then compacted. By removing particles, which are smaller than 150 μm, an essentially "dust-free" nicotine-containing granulate is obtained. If additives, such as sweeteners, binding agents, separating agents, lubricants, coloring agents, flavor additives, acids, effervescent agents, antioxidants, glidants and/or preservatives, or solvents are included, they are preferably mixed with the other components in step (a).

Preferably, steps (a) to (c) can be performed fully automatically in a closed containment. As the final product is a granulate material, which does not get dispersed in the air, cleaning of the machinery after the production is much easier and the safety measures to be taken are much less elaborate than for previously known, dust raising nicotine-containing products. In addition, the nicotine-containing granulate material of the present invention may be produced without the use of solvents, thus avoiding drying of the product and thermal stress. The product can be obtained in a continuous, one-pot process.

In a preferred embodiment, the method for producing a nicotine-containing granulate further comprises the step of
(d) recycling the small particles removed in step (c) and adding them to the mixture of step (a).

By recycling the small particles, the amount of waste material produced is significantly reduced or even completely avoided, thus also lowering the costs for starting material and for waste disposal. This is especially important because of the high toxicity of nicotine and nicotine derivatives.

In a further preferred embodiment, the nicotine-containing granulate is produced continuously. By rendering the production continuous, production times are optimized and the cleaning effort necessary is minimized.

Most preferably, the nicotine-containing granulate produced by the method according to the present invention is a nicotine-containing granulate according to claim 1.

In a further aspect, the present invention also relates to the use of the nicotine-containing granulate according to claim 1 for the preparation of a nicotine-containing pharmaceutical product, preferably for a nicotine-containing pharmaceutical product intended for oral or transdermal administration.

EXAMPLES

Example 1: Preparation of a Granulate for the Production of Lozenges, Sachets or Chewable Tablets 15.0 wt % of nicotine bitartrate, 83.5 wt % of Maltodextrin, 0.25 wt % of Acesulfam-K, 0.25 wt % of aspartame, and 1.00 wt % of magnesium stearate were mixed in a free fall mixer to obtain a homogenous mixture of the components. The mixture was compacted in a roller compactor (Powtec RC 100×20) to produce granules under a pressure of 78 bar; the feeding screw rotating at 25 rpm and the compacting rolls at 4 rpm.

The compacted granules were ground in a sieving machine (1.0 mm) and separated into the desired particle size range (e.g. 250-1000 μm) using a screen oscillating at 40 rpm. The small particles that were screened off were recycled and compacted once again, until the entire material was converted to the granulate of the desired particle size. The obtained granulate was homogenously compacted, hard, and well soluble.

The granulate may be mixed with additional components, such as flavor additives or lubricants, and be used, for instance, for the production of nicotine-containing lozenges or chewable tablets.

Example 2: Preparation of a Granulate for the Production of Chewing Gums

A granulate containing 15 wt % of nicotine polacrilin, 84 wt % of xylitol, and 1.0 wt % of magnesium stearate was prepared according to the procedure described in example 1. The thus obtained granulate is suitable for the production of nicotine-containing chewing gums.

Example 3: Preparation of a Granulate for the Production of Tablets or Coated Tablets A granulate containing 25 wt % of nicotine betadex, 74 wt % of crospovidone, and 1.0 wt % of magnesium stearate was prepared according to the procedure described in example 1.

The thus obtained granulate is suitable for the production of nicotine-containing tablets or coated tablets.

Example 4: Properties of the Nicotine-Containing Granulate

The granulates obtained in examples 1 to 3 are white, solid products, which are well suited for their further processing to pharmaceutical or nutritional goods.

The granulate such obtained exhibits a bulk density of 0.55 g/ml, an angle of repose of about 35°, and a flow rate of 5 g/s.

The invention claimed is:

1. A method for producing a nicotine-containing granulate, the method comprising the steps of:
   (a) mixing nicotine or a pharmaceutically acceptable nicotine derivative with an excipient;
   (b) compacting the mixture obtained in step (a) in a roller compactor to produce granules; and
   (c) screening the granules obtained in step (b) to remove granules that have a particle size smaller than 250 μm, wherein
   the granulate has a bulk density of at least 0.5 g/ml.

2. The method for producing a nicotine-containing granulate according to claim 1, the method further comprising the step of:
   (d) recycling the small granules removed in step (c) and adding them to the mixture of step (a).

3. The method for producing a nicotine-containing granulate according to claim 1, wherein the nicotine-containing granulate is produced continuously.

4. A method for producing a nicotine-containing granulate comprising a homogenous mixture of 1-50 wt % of nicotine or a pharmaceutically acceptable nicotine derivative and 50-99 wt % of an excipient, wherein the granulate has a particle size of at least 250 μm, the method comprising the steps of:
   (a) mixing nicotine or the pharmaceutically acceptable nicotine derivative with the excipient;
   (b) compacting the mixture obtained in step (a) in a roller compactor to produce granules; and
   (c) screening the granules obtained in step (b) to remove granules that have a particle size smaller than 250 μm, wherein
   the granulate has a bulk density of at least 0.5 g/ml.

5. A nicotine-containing pharmaceutical comprising the nicotine-containing granulate obtained by the method according to claim 1.

6. The nicotine-containing pharmaceutical according to claim 5, wherein the pharmaceutical is suitable for oral administration.

7. The nicotine-containing pharmaceutical according to claim 5, wherein the pharmaceutical is suitable for transdermal administration.

8. The method for producing a nicotine-containing granulate according to claim 1, wherein a homogenous mixture of 1-50 wt % of nicotine or the pharmaceutically acceptable nicotine derivative and 50-99 wt % of the excipient is obtained in step (a).

9. The method for producing a nicotine-containing granulate according to claim 1, wherein granules that have a particle size smaller than 500 μm are removed in step (c).

10. The method for producing a nicotine-containing granulate according to claim 1, wherein granules that are larger than 2000 μm are removed in step (c).

11. The method for producing a nicotine-containing granulate according to claim 1, wherein a homogenous mixture of 10-30 wt % of nicotine or the pharmaceutically acceptable nicotine derivative and 70-90 wt % of the excipient is obtained in step (a).

12. The method for producing a nicotine-containing granulate according to claim 1, wherein the pharmaceutically acceptable nicotine derivative used in step (a) is a solid nicotine salt or complex.

13. The method for producing a nicotine-containing granulate according to claim 1, wherein the excipient used in step (a) is selected from the group consisting of monosaccharides, disaccharides, hydrated or non-hydrated oligosaccharides, monosaccharide alcohols, disaccharide alcohols, starch, starch derivatives, cellulose, cellulose derivatives, inulin, sugar alcohols, calcium carbonate, calcium hydrogenphosphate, maltodextrins, polysaccharides, and combinations thereof.

14. The method for producing a nicotine-containing granulate according to claim 13, wherein the excipient used in step (a) is selected from the group consisting of saccharose, lactose, glucose, fructose, xylose, starch, sorbit, mannit, xylit, sugar alcohols, cellulose, calcium carbonate, calcium hydrogenphosphate, maltodextrin, and combinations thereof.

15. The method for producing a nicotine-containing granulate according to claim 1, wherein prior to the mixing in step (a), sweeteners, binding agents, separating agents, lubricants, coloring agents, flavor additives, acids, effervescent agents, antioxidants, glidants and/or preservatives are added.

16. A nicotine-containing granulate that is obtained by the method of claim 1.

17. The method for producing a nicotine-containing granulate according to claim 12, wherein the solid nicotine salt or complex is selected from the group consisting of nicotine bitartrate, nicotine polacrilin, nicotine betadex, nicotine polacrilex, and combinations thereof.

18. The method for producing a nicotine-containing granulate according to claim 1, wherein in (c), granules that have a particle size of 250 μm or smaller are removed.

19. The method for producing a nicotine-containing granulate according to claim 4, wherein the granulate has a particle size of greater than 250 μm, step (c) comprises screening the granules obtained in step (b) to remove granules that have a particle size of 250 μm or smaller.

* * * * *